United States Patent [19]

Lancaster et al.

[11] Patent Number: 4,932,398
[45] Date of Patent: Jun. 12, 1990

[54] ANAESTHETIC VAPORIZER INTERLOCK SYSTEM AND CONNECTOR FOR ANAESTHETIC APPARATUS

[75] Inventors: Adrian Lancaster, Exeter; Peter W. Alderton, Chagford; William T. Quick, Cullompton, all of England

[73] Assignee: Dentsply Limited, Weybridge, England

[21] Appl. No.: 290,484

[22] Filed: Dec. 23, 1988

[51] Int. Cl.⁵ .............................................. A61M 11/00
[52] U.S. Cl. ............................ 128/200.14; 128/200.19; 137/637.1; 74/483 R; 74/484 K; 251/149.9
[58] Field of Search ...................... 128/202.27, 203.12, 128/202.22, 200.24, 200.14, 200.19, 200.23, 203.25, 203.28; 137/637.1; 74/483 R, 483 K; 261/DIG. 65; 251/149.9

[56] References Cited

U.S. PATENT DOCUMENTS

| | | |
|---|---|---|
| 64,292 | 4/1867 | Douglas . |
| 149,728 | 4/1874 | Diehl et al. . |
| 263,415 | 8/1882 | Lightburne, Jr. . |
| 328,427 | 10/1885 | Nusbeck . |
| 337,867 | 3/1886 | Richards . |
| 551,733 | 12/1895 | Mullenhoff . |
| 796,306 | 8/1905 | Exley . |
| 1,026,269 | 5/1912 | Knauff . |
| 1,117,762 | 11/1914 | Barcus . |
| 1,256,666 | 2/1918 | Douglas . |
| 1,307,273 | 6/1919 | Salley . |
| 1,549,858 | 11/1924 | Evans . |
| 1,744,367 | 6/1926 | Loache . |
| 1,762,572 | 8/1928 | Davidson . |
| 1,871,370 | 6/1929 | Jacques . |
| 4,246,115 | 1/1981 | Swank . |
| 4,307,718 | 12/1981 | Schreiber . |
| 4,308,865 | 1/1982 | Hay . |
| 4,346,701 | 8/1982 | Richards ................ 128/200.14 |
| 4,351,327 | 9/1982 | Rinne et al. . |
| 4,434,790 | 3/1984 | Olesen . |
| 4,463,754 | 8/1984 | McDonald . |
| 4,493,318 | 1/1985 | Mohr et al. . |
| 4,546,794 | 10/1985 | Ball . |
| 4,759,358 | 7/1988 | Gregory ................ 128/200.14 |

FOREIGN PATENT DOCUMENTS 77160 8/1902 Canada .
77262 8/1902 Canada .
79816 3/1903 Canada .

(List continued on next page.)

OTHER PUBLICATIONS

Newly published ISO and IEC Standards–Standards Action–Jul. 31, 1987 p. 9 of 12 pages.
Survey Report–Results of the Canadian Anaesthetists' Society Opinion Survey on Anaesthetic Equipment. (Philip D. Neufeld PH D., David L. Johnson PH D pp. 469–473 Can Anaesth Soc J 1983 No. 5.
Technical communications–Safety of Anaesthesia Breathing Circuit Connectors Philip D. Neufeld PHD, David L. Johnson PH d, John deVeth Can Anaesth Soc J 1983 No. 6, pp. 646–652.
Anaesthesia, 1986, vol. 41, No. 4, pp. 438–439.
Canadian Standards Association–CSA Preliminary Standard Z168.9–M1986 Breathing Systems for Use in Anaesthesia (Health Care Technology) Cover and p. 18.

Primary Examiner—Eugene H. Eickholt
Attorney, Agent, or Firm—David E. Wheeler; Edward J. Hanson, Jr.

[57] ABSTRACT

An anaesthetic apparatus having a plurality of vaporizers is provided which utilizes an interlocking device which prevents more than one vaporizer from being activated at one time. The interlock device can be used with any number of vaporizers mounted side-by-side. The interlock device comprises a cam follower which is adapted to be received in a rotating cam which is used to activate the vaporizer. The cam follower is connected to a pair of cranks which activate bars which interact with bars on adjacent interlocking devices, when one of the interlocking devices is activated, thereby locking all the other vaporizers in a inoperative position. Also provided is a safety lock connector which is used for connecting hose to an anaesthesia apparatus.

11 Claims, 8 Drawing Sheets

FOREIGN PATENT DOCUMENTS

| | | |
|---|---|---|
| 97223 | 1/1906 | Canada . |
| 189092 | 3/1919 | Canada . |
| 378334 | 12/1938 | Canada . |
| 988552 | 9/1944 | Canada . |
| 999326 | 12/1945 | Canada . |
| 1004706 | 6/1947 | Canada . |
| 1058243 | 8/1954 | Canada . |
| 1105959 | 10/1954 | Canada . |
| 1133966 | 5/1955 | Canada . |
| 1158690 | 2/1961 | Canada . |
| 1166827 | 3/1966 | Canada . |
| 1181111 | 5/1970 | Canada . |
| 1183563 | 7/1970 | Canada . |
| 1187530 | 8/1970 | Canada . |
| 1188943 | 9/1970 | Canada . |
| 1204129 | 10/1970 | Canada . |
| 1205836 | 11/1970 | Canada . |
| 1209171 | 12/1970 | Canada . |
| 1222786 | 1/1971 | Canada . |
| 1226012 | 2/1974 | Canada . |
| 1385670 | 2/1974 | United Kingdom . |
| 1469246 | 4/1977 | United Kingdom . |
| 2052271 | 1/1981 | United Kingdom . |
| 2068238 | 7/1983 | United Kingdom . |
| 2070440 | 9/1983 | United Kingdom . |
| 2121691 | 1/1984 | United Kingdom . |
| 2141032 | 5/1986 | United Kingdom . |
| 2193642 | 2/1988 | United Kingdom . |
| 2060403 | 5/9181 | United Kingdom . |

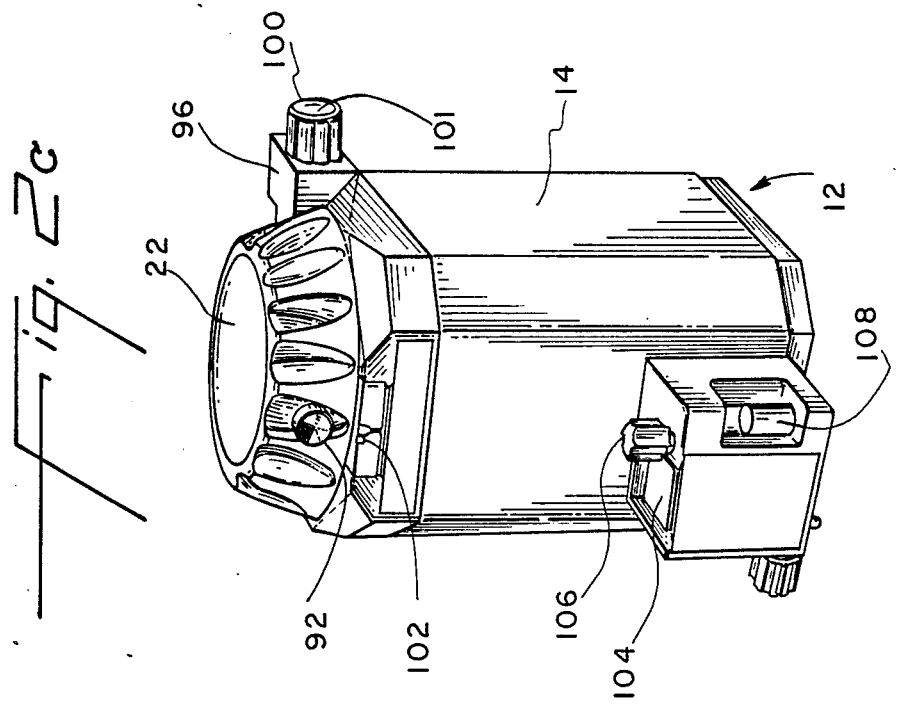
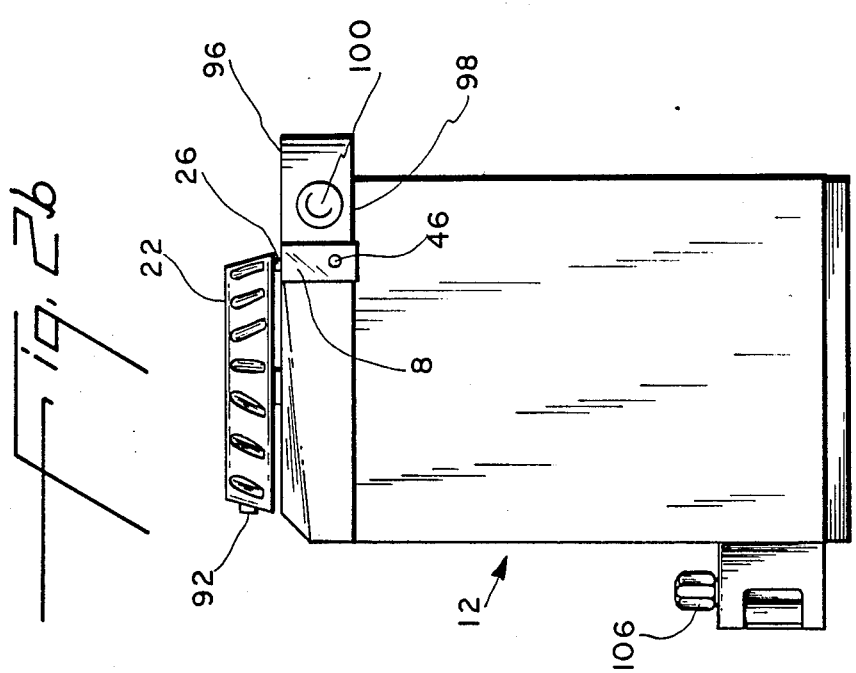

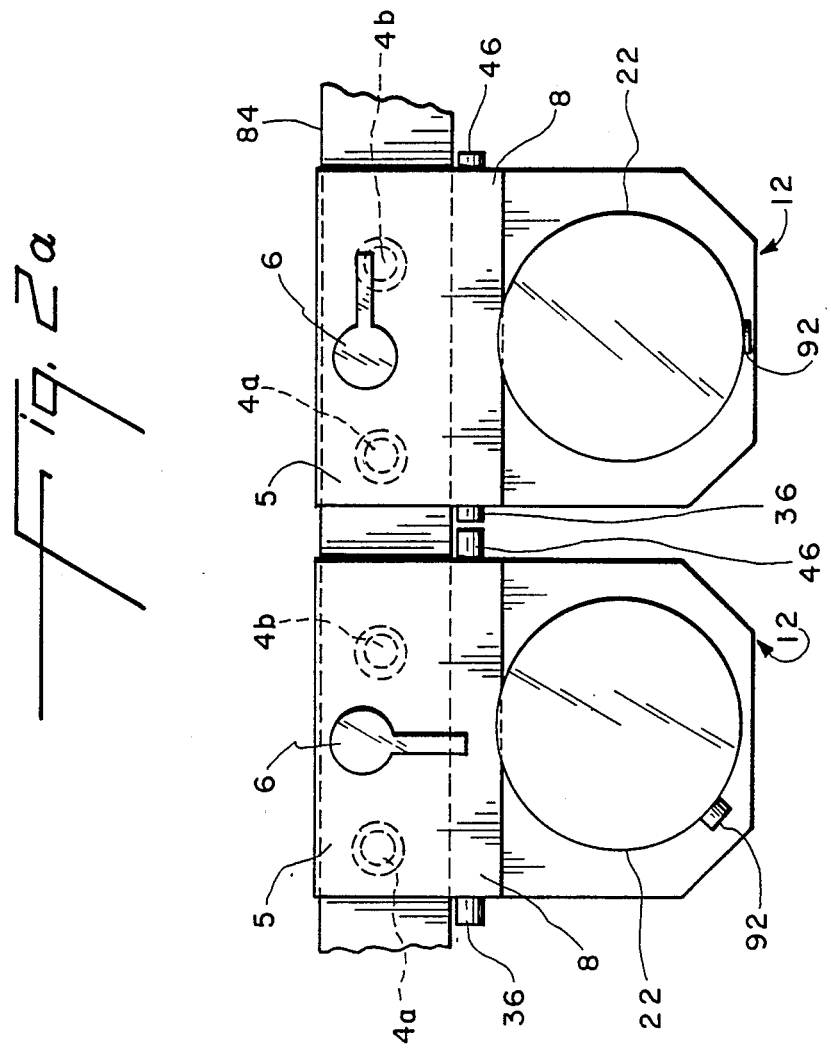

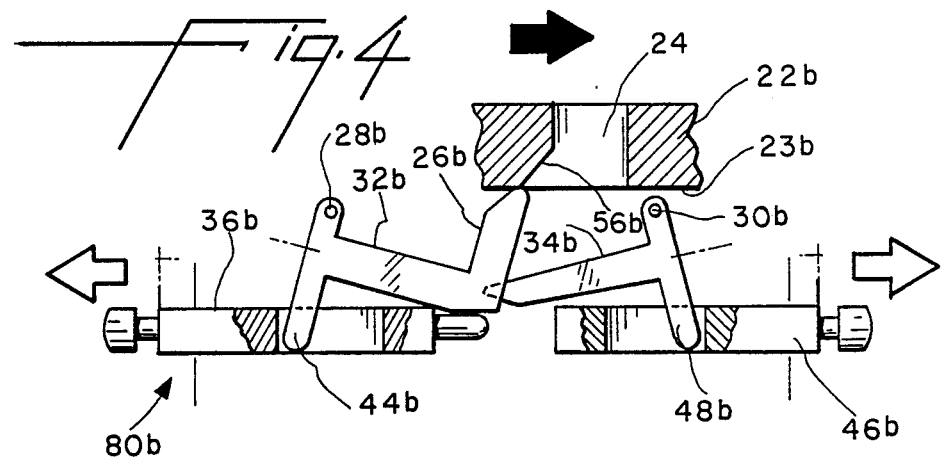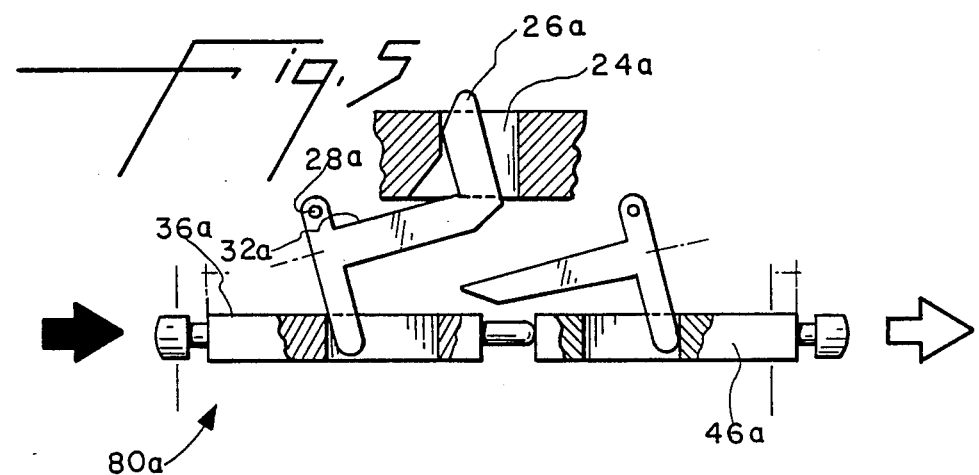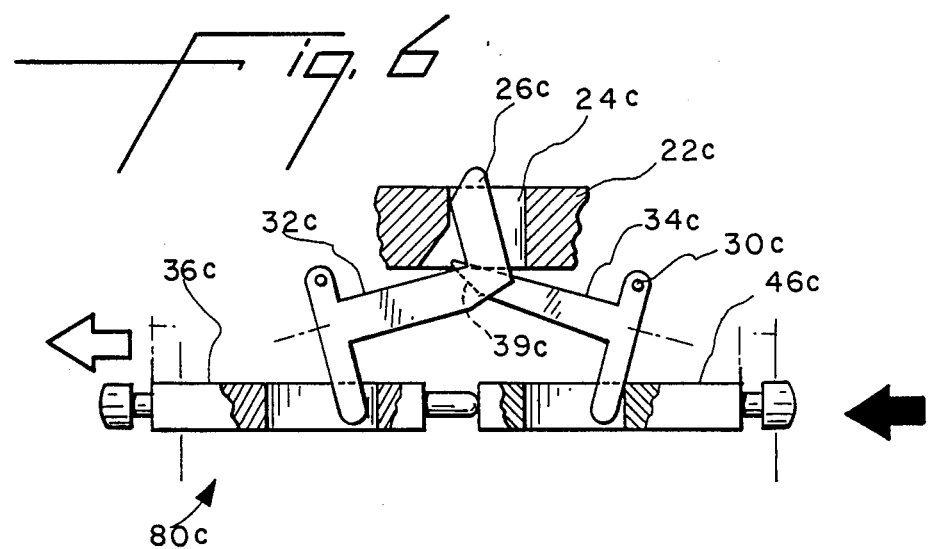

ANAESTHETIC VAPORIZER INTERLOCK SYSTEM AND CONNECTOR FOR ANAESTHETIC APPARATUS

BACKGROUND

The invention relates to anaesthesia machines and more particularly to interlock devices for anaesthesia machine vaporizers and locking devices for connecting tubing to an anaesthesia machine.

Anaesthesia equipment typically consists of a trolley on which are mounted cylinders containing medical gases such as oxygen, air and nitrous-oxide and associated pressure regulating valves. Anaesthetic agents such as halothane and isoflurane are commonly administered by passing a carrier gas such as air or oxygen mixed with nitrous-oxide through a vaporizer which contains the liquid anaesthetic agent.

Conventional anaesthesia apparatus or machines commonly incorporate two or more separate vaporizers. Each vaporizer is arranged to dispense a metered amount of anaesthesia vapor into the patient breathing circuit or fresh gas line. These vaporizers may contain different anaesthetic agents so that the same equipment can be used for a series of surgical operations to supply the particular anaesthetic agent desired. The arrangement of more than one vaporizer on the same anaesthetic equipment does, however, lead to the possible risk that more than one vaporizer could accidentally be connected to the gas administration circuit at the same time. In order to cope with this problem, various interlock systems have been proposed in order to prevent more than one vaporizer being operated at the same time. For example, U.K. patent specifications Nos. 2052271 and 2193642 describe one such interlock system. While the interlock arrangements described in these two patent specifications are satisfactory with the type of hook-on vaporizers described in U.K. patent specification No. 1385670, there is at least one other widely used system in use for connecting vaporizer units to a gas administration circuit. There is, therefore, a need for a vaporizer interlock system which can be adapted for use with more than one type of gas administration system.

While the construction of commercially available vaporizers varies from manufacturer to manufacturer, the most common type of vaporizer comprises a canister including a reservoir for the anaesthesic agent, valve means and a rotatable dial coupled to the valve means for adjusting the valve means to establish the vaporizer concentration levels. Such machines may include a rotary dial for adjusting the opening of a valve in the vaporizer to divide the gas flow in the vaporizer in accordance with the dial setting. Part of the gas flow passes through a by-pass, without entering the vaporizer chamber (where the anaesthetic agent is located), while the remaining portion of the gas flow passes through the vaporizer chamber for saturation by anaesthesia vapor. The gas flow which is saturated with the vapor is then combined with the by-pass gas flow so that the gas leaves the vaporizer carrying a set concentration of anaesthesia. The introduction of the gas carrying anaesthesia vapor into the fresh gas line is effected by an outlet valve under the control of a separate lock-/unlock switch. A pair of rotary cams and a pivoting lever are provided to serve as an interlock to insure that the outlet of the vaporizer is opened when the rotary dial is adjusted to any particular setting and to prevent the adjustment dial from being rotated to any setting when the lock/unlock switch is closed, thereby precluding any gas from passing into the vaporization chamber when the outlet of the vaporizer is closed.

Many such interlock systems provide an interlock only between two vaporizers of one connector type.

It is an object of this invention to provide an improved interlock system which can be used with two or more vaporizers with the added feature that each of the vaporizers may be a different connector type.

The present invention also relates to a safety lock hose connector for use with the anaesthetic apparatus of the invention. Typical hose connectors for anaesthetic breathing systems, for example, comprise a tapered, hollow male member for insertion into a correspondingly internally tapered female member. The size and degree of taper of such connectors are covered by various national and international standards.

Commonly the male member is made of metal (generally stainless steel) and the female member is made of metal or of plastic material or, as described in GB-A-No. 1396096, may comprise a metal sleeve housed within a plastic housing.

One problem which can occur with such connectors is accidental disconnection and, clearly as can be appreciated, this can give rise to potentially severe problems. It is an object of the present invention to provide a hose connector having a securing system serving to prevent accidental disconnection but allowing for simple and rapid intentional connection and disconnection.

Accordingly, the invention comprises an interlock system for use with a plurality of vaporizers which, on activation of one of the vaporizers, prevents activation of any number of vaporizers to the right or the left of the activated vaporizer.

The invention also provides a hose connector comprising an externally tapered male connection member and an internally tapered, generally tubular, female connection member in which the male member is provided with a collar which defines, together with the male member, an annular recess for reception of the end of the female member, and the inner wall of the collar defining the recess has at least one helical groove extending from the free end of the collar towards the fixed end thereof: and the female member is provided with one or more external lugs or pins for engaging with the groove in the collar.

The invention also provides hose to hose connections on an anaesthetic apparatus in which hose is connected to the apparatus by means of the connector of the invention.

SUMMARY

An anaesthesia machine having a plurality of vaporizers for introducing a metered concentration of vapor into a gas flow when in-circuit is provided, each said vaporizer comprises rotatable adjustment cam means for opening the vaporizer, and establishing the vapor concentration introduced thereby. Associated with each vaporizer is an improved interlock device which prevents activation of the vaporizer when another of the vaporizers is activated. The interlock device comprises a cam follower which engages a notch in the rotatable adjustment cam, said cam follower comprising one end of a substantially Z shaped (first) sprung crank which is rotatable about a first fixed pin, the distal end of said sprung crank being engaged in a slot in a first sliding bar; a second substantially T shaped crank which is rotatable about a second fixed pin, having a first end impinging on said sprung crank, the distal end of said second crank being engaged in a slot in a second sliding bar; said first and second sliding bars having inboard ends which have abutting contact with each other when the vaporizer is inactivated, and outboard ends which may have abutting contact with the outboard ends of a similar sliding bar on adjacent vaporizers. The cam followers, by action with the cranks and the sliding bars cooperate with each other so that when the adjustment cam means of the vaporizers are off, one of the cam followers can be moved out of engagement with its associated notch by the mere rotation of its associated adjustment cam means to open the vaporizer and establish any vapor concentration, while such rotation locks all the other cam followers in position in engagement with its associated notch to lock its associated adjustment cam means closed.

The interlock device is demountable and may be easily installed on existing anaesthetic apparatus manufactured by, especially, M. I. E. Dentsply of Exeter, England.

The vaporizer body is preferably provided with a platform portion which is adapted to receive a mounting block for connection to the gas supply circuit. Ports are provided in the platform for connection with the interior of the vaporizer and for sealing the ports to corresponding ports in the mounting block. The mounting block may be a unit which is adapted to hook onto a gas supply bar in a similar way to that described in U.K. Patent specification No. 1385670. Alternatively, the mounting block may incorporate conventional taper tubular connector parts so that the vaporizer may be connected directly to a gas supply circuit.

Also provided for use with the anaesthetic machine of the invention is a quick connect locking device for connecting hoses to the anaesthetic machine, and hose to hose. The quick connect locking connector comprises a male tapered connector having a split collar locking ring attached to said apparatus, and a bayonet type female connector attached to said breathing tube, said female connector having at least one lug affixed to its outer circumference adjacent to the connector mouth adapted to engage said split collar, said split collar having at least one locking groove at a precise angle and dimensions suitable to accommodate at least one lug on said female connector.

The split collar locking ring is adapted to be easily attached to existing anaesthetic apparatus.

DESCRIPTION OF THE DRAWINGS

FIG. is a front elevational view of an anaesthesia machine.

FIG. 2a is a plan view showing a pair of vaporizers mounted in hook-on fashion on a gas supply bar of an anaesthetic machine.

FIG. 2b is a side elevation of one vaporizer connected to a gas supply line having conventional taper connections.

FIG. 2c is a perspective view of a single vaporizer similar to that shown in FIG. 2b, from the rear quarter, but without an interlock unit.

FIG. 4 is an illustration of the position of the working parts in the interlock system when the vaporizer is activated.

FIG. 5 illustrates the affect of the interlock system of an activated vaporizer on the interlock system of a vaporizer to the right of said activated vaporizer.

FIG. 6 illustrates the affect of the interlock system of an activated vaporizer on the interlock system of a vaporizer to the left of said activated vaporizer.

DETAILED DESCRIPTION OF THE INVENTION

Figure 1:
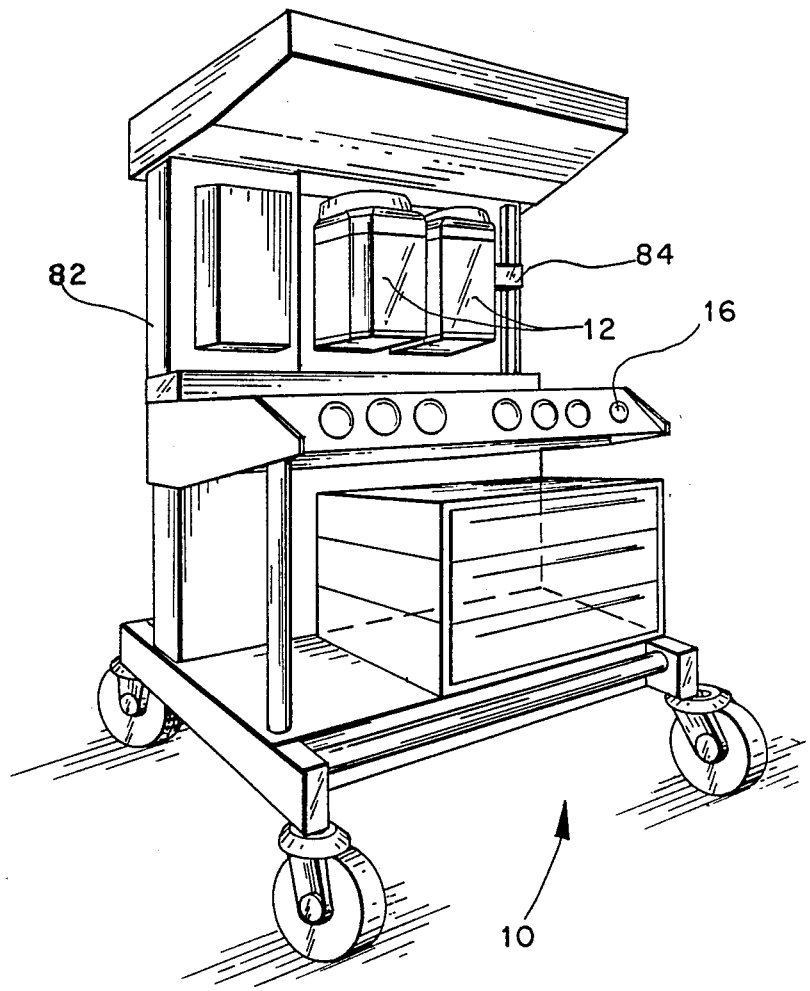

Referring now to FIG. 1 an anaesthesia machine 10 of the invention is illustrated having two vaporizers 12.

Figure 2:
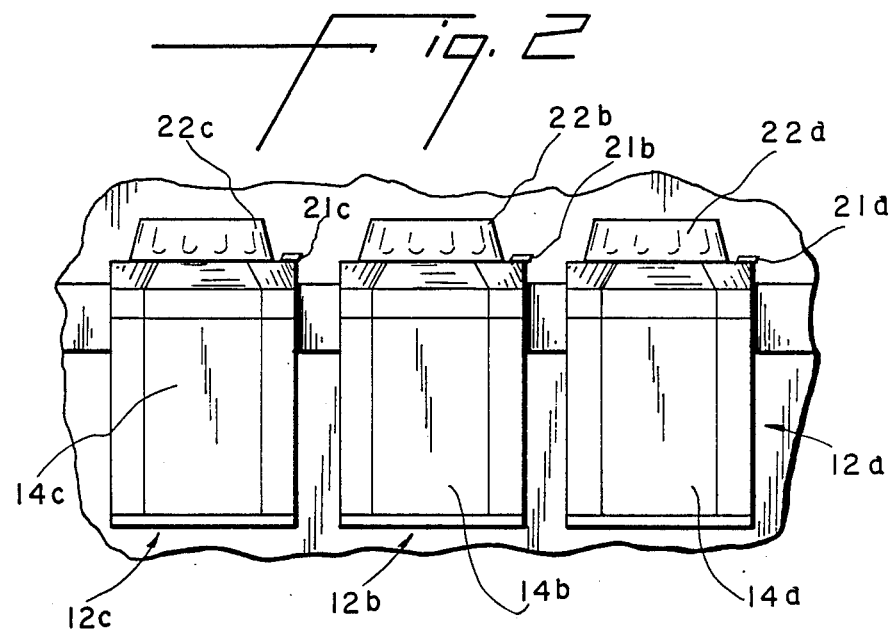
FIG. 2 is an illustration of sharing an embodiment having three side by side vaporizers on an anaesthesia machine.

With reference now to FIG. 2, the relationship of vaporizers 12 is illustrated in an embodiment where more than two vaporizers are used.

Referring now to FIGS. 2, 2a, 2b and 2c, and in particular to FIGS. 2a and 2b, the arrangement comprises vaporizers which are mounted in hook-on fashion on a gas supply bar 84 of the kind described in British Patent Specification No. 2052271, incorporated herein by reference. As described in the above-mentioned Patent, tubular ports 4a and 4b are upstanding on the gas supply bar 84 and are received in corresponding recesses in a housing 5. When the ports 4a and 4b are located in their corresponding recesses, the vaporizers may be locked in position on the supply bar 84 by rotating the knob 6 to the position shown in the left-hand vaporizer. Carrier gas can be admitted into the vaporizers by releasing the cam dial lock 92 and rotating the cam dial 22 of the vaporizers whereupon vapor will be passed, together with carrier gas from the vaporizer, through port 4b into the gas supply bar 84. This arrangement is essentially described in U.K. Patent Nos. 1385670 and 2052271, both incorporated herein by reference. In accordance with the invention, the vaporizers are also provided with an interlock unit whereby as soon as one of the vaporizers is operated, it is impossible to admit carrier gas to an adjoining vaporizer. The interlock mechanism is located in a unit 8 forming a web-like enclosure on each vaporizer. Interlock units 8 (FIG. 2a) include bars 36 and 46 which are arranged to come into contact with an adjacent pin 9 or 10 as soon as one vaporizer is operated. Thus in the arrangement shown in FIG. 2a, the vaporizer on the left-hand side has been opened to the carrier gas by pressing the release button 92 and turning the cam dial 22 in a counterclockwise direction.

With reference now to FIG. 2b, interlock unit 8 includes a cam follower 26 which engages in a notch 24 in a rotating cam forming part of dial 22 of vaporizer 12. Because interlock unit 8 makes direct contact with the rotating cam 22, it is largely independent of the remainder of the vaporizer operating mechanism and can thus be made as a demountable separate unit and conveniently installed between the vaporizer and the connector 96 for connecting the vaporizer to a supply of carrier gas.

Interlock unit 8 conveniently consists of a housing holding the actuating mechanism which is screwed or otherwise fixed to the body of the vaporizer. Because the interlock unit is essentially independent of the vaporizer operating mechanism and occupies only a thin web-like housing, it can conveniently be installed between the vaporizer body and the carrier gas mounting block, whether of the plug-in type or of the taper-connection type. In FIGS. 2b and 2c, in fact, the connector 96 is of the taper joint type and consists of a body member having ports aligned with corresponding connections in a platform part 98 of the body of the vaporizer. Tapered tubular connectors 100 are provided on the mounting block for connection to the adjacent vaporizer or to the next stage in the gas supply circuit.

FIG. 2c shows further features of the vaporizer which are generally conventional but indicates the connection of the vaporizer to the mounting block 96. A gauge 102 shows the degree by which the vaporizer is open and is normally calibrated to give a concentration of anaesthetic agent in the carrier gas. The vaporizer is filled by adding liquid anaesthetic to the tray 104 and operating stopcock 106. Sight tube 108 shows the amount of anaesthetic in the vaporizer.

Figure 3:
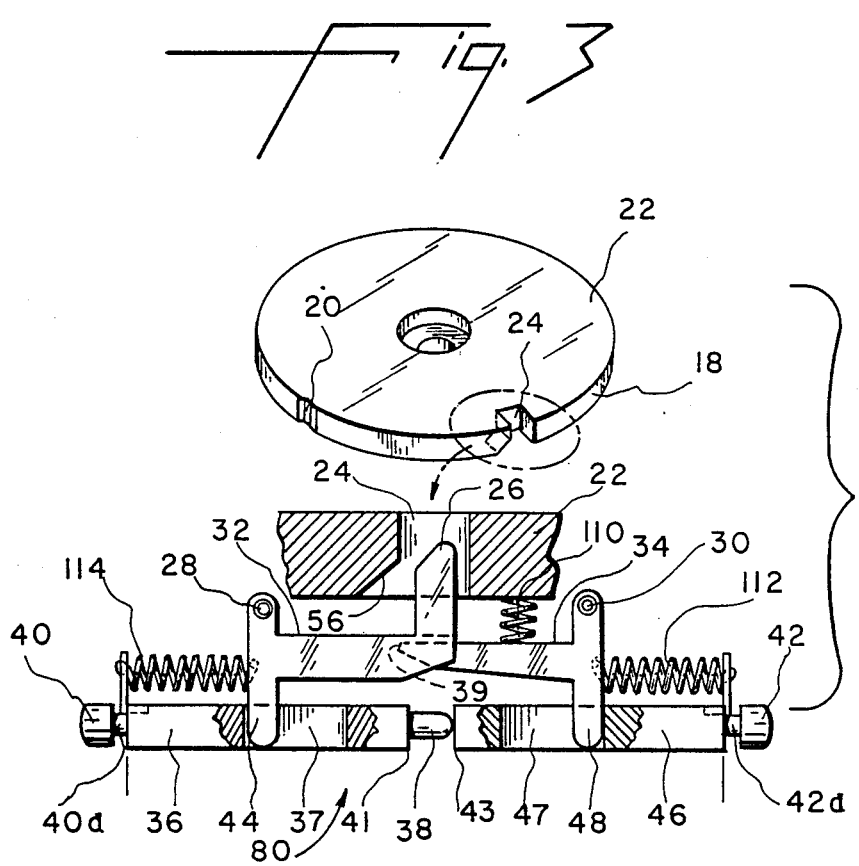
FIG. 3 is an illustration of an interlock system associated with each vaporizer.

With reference to FIG. 3 each of the vaporizers 12a, 12b and 12c is of conventional internal construction coupled to a vapor concentration adjustment cam plate dial 22. Each vaporizer comprises a canister 14 containing the anaesthesia vapor to be dispensed and the means for metering the same into the gas line 100 (FIG. 2c) of machine 10. The concentration of the anaesthesia vapor provided by each of the vaporizers is determined by the setting of the vapor concentration adjusting cam plate dial 22. As can be seen, each cam plate dial 22 is a generally disk-shaped member having a circular, outer surface 18. The outer surface 18 includes plural indicia 20 marked thereon corresponding to the vapor concentration provided by the vaporizer. The canister 14 includes an arrow or pointer indicia 21 to indicate the particular vapor concentration setting as established by the vaporizer. When the off mark of indicia 20 is aligned with the arrow 21, the vaporizer is inoperative. The rotation of the cam plate dial 22 counterclockwise opens the vaporizer to introduce vaporized gas into a patient breathing circuit 52 (See FIG. 1 and 9). The concentration level established by the setting of the cam plate dial 22 is displayed by the indicium 20 disposed opposite to pointer 21.

With reference now to FIGS. 3–6, it will be noted that each cam plate dial 22 includes a respective notch 24 in its circular peripheral surface 18. Notch 24 is adapted to receive cam follower 26 of interlock device 80. Interlock device 80 comprises substantially Z shaped sprung crank 32, which is rotatable around fixed pin 28, the first end of which comprises cam follower 26, and distal end 44 of which is engaged in slot 37 of sliding bar 36; substantially T shaped crank 34 which impinges on sprung crank 32 at contact point 39, helping to retain cam follower 26 in notch 24, and which rotates on fixed pin 30, distal end 48 of which is engaged in slot 47 of sliding bar 46; and sliding bars 36 and 46 which comprise inboard ends 41 and 43, respectively, which have an abutting relationship when the associated vaporizer is in an off condition, outboard ends 40 and 42, respectively, which may abut similar sliding bars on adjacent vaporizers, and slots 37 and 47 for receiving distal ends 44 and 48, respectively, of sprung crank 32 and T shaped crank 30, respectively. Crank 32 is biased into the position shown in FIG. 3 by spring 110. Springs 110 and 112 are provided to assure a balanced rest position for crank 32 and 34. Sliding bars 36 and 46 may optionally have a length adjustment means associated therewith by which the length of the sliding bars may be adjusted to ensure a proper abutting relationship with each other. Sliding bars 36 and 46 may optionally have length adjustment means 40 and 42 associated therewith by which the length of sliding bars may be adjusted to ensure a proper abutting relationship with the sliding bars of adjacent vaporizers. In the illustrated embodiment adjustable extension 38 is provided on inboard end 41 of sliding bar 36, and adjustable extensions 40a and 42a are provided on the outboard ends of sliding bars 36 and 46, respectively. Cam follower 26 is adapted for reciprocation into or out of a respective notch 24 in the cam dial 22 of an associated vaporizer 12.

In the illustrated embodiment, slide bars 36 and 46 are spring loaded to maintain tension between crank 32 and slide bar 36, between crank 34 and slide bar 46, and between slide bar 36 and slide bar 46. Distal end 44 of crank 32 and distal end 48 of crank 34 are engaged in slot 37 of slide bar 36 and slot 47 of slide bar 46 respectively in a manner that ensures that the motion of only one of the cranks may control the movement of the slide bar. For example, when crank 34 causes slide bar 46 to move to the right, crank 32 moves right in slot 37 without exerting any force on slide bar 36. Similarly, when crank 32 causes slide bar 36 to move to the left, crank 34 moves in slot 47 without exerting any force on slide bar 46. Those skilled in the art will recognize that the locking system of the invention may be activated by other mechanisms.

In the operation of anaesthetic machine 10 (FIG. 1), when it is desired to activate an anaesthetic canister 12, the operator merely turns cam dial 22 to the desired position, which forces cam follower 26 out of notch 24 (See FIG. 4). For purposes of illustration, it is assumed that the operator activates vaporizer 12b (See FIG. 2). Referring now to FIG. 4, when cam 22b is rotated counter-clockwise, beveled edge 56b of notch 24b forces cam follower 26b to slide out of notch 24b and slide under bottom surface 23b of cam dial 22b. Because of the movement of cam follower 26b, sprung crank 32b rotates clockwise on fixed pin 28b which causes distal end 44b to move to the left, thereby forcing sliding bar 36b to the left. Similarly, the downward motion of cam follower 26b causes substantially T-shaped crank 34b to rotate on fixed pin 30b in a counter-clockwise motion, which causes distal end 48b, and consequently sliding bar 46b to move to the right.

With reference now to FIG. 5, the interlock system 80a associated with vaporizer 12a to the right of vaporizer 12b, causes vaporizer 12a to lock, preventing its operation. Vaporizer 12a is locked because the movement of sliding bar 36a to the right, caused by the motion of sliding bar 46b, which causes sprung crank 2a to rotate counter-clockwise on fixed pin 28a, causes cam follower 26a to push further into notch 4a. Because of the relationship of sliding bars on each of the vaporizers to each other, cam follower 26a cannot be removed from notch 24a until cam follower 26b returns to notch 24b.

Because of the movement of slide bars 36a and 46a to the right, the interlock system of any vaporizer that could theoretically be to the right of vaporizer 12a is affected in exactly the same manner as vaporizer 12a.

In a slightly different manner, vaporizer 12c, to the left of vaporizer 12b, is locked in an inactivated condition when vaporizer 12b is turned on. In the case of vaporizer 12c, locking of cam follower 26c in cam dial 22c takes place when the leftward movement of sliding bars 36c and 46c, caused by the leftward movement of sliding bar 36b, causes T-shaped crank 34c to rotate in a clockwise direction on fixed pin 30c, causing crank 34c to push against crank 32c at contact point 39c, forcing cam follower 26c into notch 24c. Cam follower 26c cannot be removed from notch 24c as long as sliding bars 36c and 46c remain in their displaced condition, and sliding bars 36c and 46c cannot return to their original position until cam follower 26b is returned to notch 24b.

The motion of slide bars 36c and 46c to the left has the exact same effect on any vaporizer that may be to the left of vaporizer 12c.

Accordingly, the interlock mechanism of the invention can interlock any desired number of vaporizers.

The invention has the advantage that standard vaporizers (Manufactured by M. I. E.) may be readily adapted to an interlock system when mounted side-by-side in anaesthetic equipment. It is only necessary to modify the top of the vaporizer housing to accept the interlock unit and to provide the valve operating wheel with a recess which is capable of receiving the locking member of the interlock unit. Apart from this interaction, the interlock unit is independent of the rest of the vaporizer and preferably occupies a thin web-like space between the mounting block and the top part of the vaporizer housing. The interlock unit may be replaced by a spacer if it is desired to mount the vaporizer singly in anaesthetic equipment or without providing an interlock feature. Accordingly, the interlock unit can be easily installed on existing M. I. E. anaesthetic apparatus.

Figure 7:
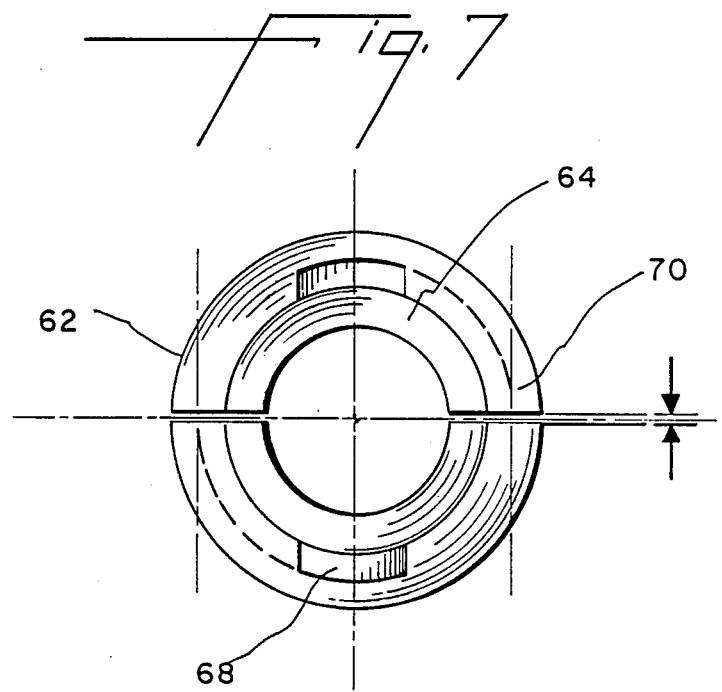
FIG. 7 illustrates an end view of a split collar locking ring of the invention.
Figure 8:
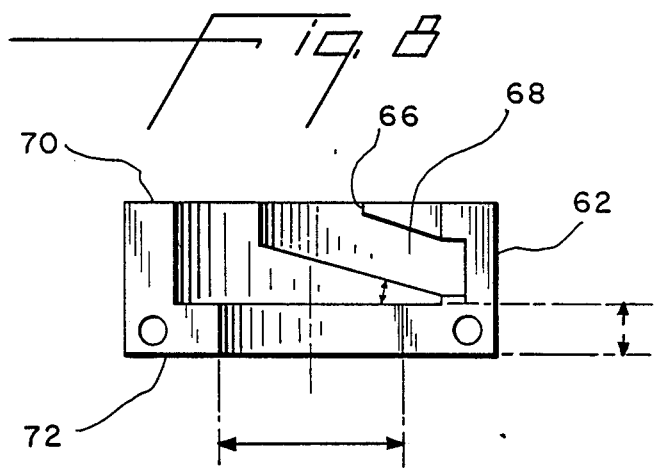
FIG. 8 illustrates a side, cutaway view of a split collar locking ring of the invention.
Figure 9:
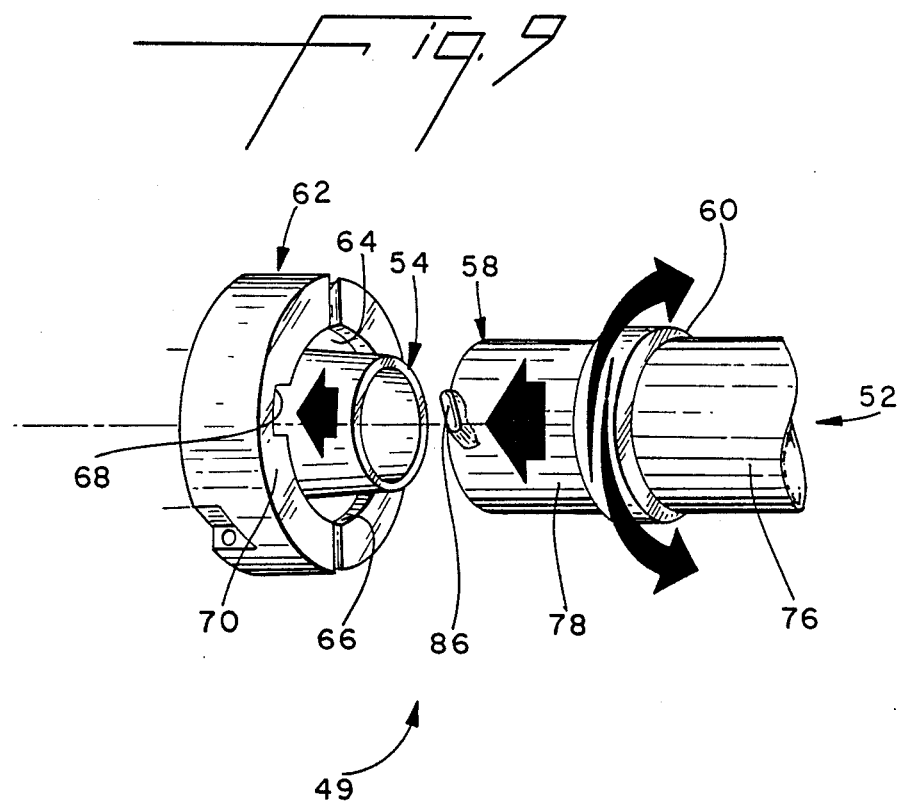
FIG. 9 illustrates a locking device for attaching a breathing tube to said anaesthetic machine, or hose to hose.

With reference now to FIGS. 7–9, the present invention also provides a safety lock hose connector which prevents inadvertent disconnection of the breathing tube to the anaesthetic apparatus. The safety lock hose connector 49 comprises a male member 54 attached to anaesthetic apparatus 10 (as indicated at 100) and is provided with a split ring locking collar 62 attached thereto, the collar 62 and the outer surface of the male member together define an annular recess 64 and the inside wall 66 of collar 62 is provided with a pair of helical or spiral grooves 68 extending from the free outer end 70 of the collar towards the fixed end 72 of the collar. Tubular female member 58 having an internally tapered portion (not shown) and connected to flexible hose 76 is adapted to mate with male member 54. The outer wall 78 of female member 58 is provided with lugs 86 for engagement in groove 68 in collar 62. The safety lock connector provides metal to metal contact between the hose and the machine, which helps prevent the build-up of static electricity, which potentially could cause a spark.

In its operation, with reference to FIG. 9, female member 58 is brought into contact with male member 54 and loosely engaged therewith. Further forward movement (by hand) of female member 58 causes lugs 86 thereon to engage in the open ends of grooves 68 in collar 62. By rotating grip ring 60 in a clockwise direction the lugs 86, guided by the spiral locking groove 68, draw female member 58 into further contact with male member 54 until the two members lock to form a gas-tight seal. The twisting motion imparted to the female connection member by the locking ring grooves ensures good frictional lock between the two members. Axial and radial movement of the female connector is prevented by the friction between lugs 86 and the walls of groove 68 and the friction between the male and female tapered surfaces. It should be noted that operation of the connector in accordance with the invention can simply be carried out as a one-handed operation as, indeed, can unlocking and disconnection of the connector which is simply affected by twisting the connector counterclockwise by hand until lugs 86 are free to be pulled outwardly of groove 68. This rotational motion breaks the friction between the two members and align lugs 86 with the apertures in the forward face of collar 62.

Since a key to the safety lock hose connector is the split ring locking collar, the safety lock can be easily installed on existing anaesthetic machines and breathing systems by merely installing the split ring locking collar on the machine.

Those skilled in the art will recognize that such a locking device can be used anywhere on an anaesthetic apparatus or breathing system where a hose connection is made.

As is apparent from the discussion in the background and in the description above, the locking mechanism of the invention provides a secure hose connection which can be easily disconnected in an emergency.

While present embodiments of the invention have been illustrated and described, it will be recognized by those skilled in the art that the present invention may be otherwise variously embodied and practiced without departing from the scope of the following claims.

What is claimed is:

1. In an anaesthetic apparatus having a plurality of vaporizers mounted in side-by-side relation, each arranged for introducing a metered concentration of vapor into a gas flow when opened, each of said vaporizers comprising rotatable adjustment means having a dial for opening said vaporizer, establishing the vapor concentration introduced thereby and closing said vaporizer, said vapor concentration being adjustable by said rotatable adjustment means, and an interlock device associated with each vaporizer unit which comprises a back bar for insuring that one of said vaporizers are rendered inoperative whenever one is opened, the improvement comprising an interlock device which comprises a rotating cam plate which acts as a control dial on said vaporizer to control the vapor concentration provided by said vaporizer, said cam plate having a peripheral notch therein adapted to receive a cam follower for locking said cam plate in position, said cam follower being one end of a substantially Z shaped sprung crank which rotates about a first fixed pin wherein rotation of said sprung crank on said first fixed pin in a first direction causes said cam follower to move from said notch thereby permitting rotation of said cam plate, a second substantially T shaped crank impinging on said sprung crank wherein said second crank rotates on a second fixed pin, wherein the distal ends of said first and second cranks engage slots in first and second sliding interlock bars in said back bar, said sliding bars being spring loaded to maintain inboard ends thereof in contact with each other, wherein rotation of said rotating cam cause rotation of said first crank in said first direction causing said second crank to rotate in the opposite direction whereby the distal ends of said first and second cranks cause said first and second sliding bars to move apart and to impinge on similar interlock bars in adjacent vaporizer units with an opposite relative motion, said opposite motion of said sliding bar on adjacent vaporizer units locking a cam follower associated therewith into a notch in the rotating cam of said adjacent vaporizer unit, thereby preventing said vaporizer unit from being activated.

2. The anaesthetic apparatus of claim 1 in which at least one of an inboard or outboard end of said sliding bar has a adjustable extension.

3. The anaesthetic apparatus of claim 2 in which one inboard end and both outboard ends have an adjustable extension.

4. The anaesthetic apparatus of claim 1 in which butting of interlock bars on said adjacent vaporizer is sufficient to prevent said vaporizer from being activated.

5. The anaesthetic apparatus of claim 1 in which the motion of the interlock bars on a first vaporizer unit causes significant motion of the interlock bars on an adjacent vaporizer unit such that a first crank on said adjacent vaporizer unit rotates in a second direction which forces and locks a cam follower associated therewith into a notch in the rotating cam of said adjacent vaporizer unit.

6. An interlock device to control a plurality of dispensing devices in side-by-side relation, said interlock device comprising a rotating cam plate which acts as a control dial on said dispensing device to control the vapor concentration provided by said dispensing device, said cam plate having a peripheral notch therein adapted to receive a cam follower for locking said cam plate in position, said cam follower being one end of a substantially Z shaped sprung crank which rotates about a first fixed pin wherein rotation of said sprung crank on said first fixed pin in a first direction causes said cam follower to move from said notch thereby permitting rotation of said cam plate, a second substantially T shaped crank impinging on said sprung crank wherein said second crank rotates on a second fixed pin, wherein the distal ends of said first and second cranks engage slots in first and second sliding interlock bars in said back bar, said sliding bars being spring loaded to maintain inboard ends thereof in contact with each other, wherein rotation of said rotating cam causes rotation of said first crank in said first direction and causes said second crank to rotate in the opposite direction whereby the distal ends of said first and second cranks cause said first and second sliding bars to move apart and to impinge on similar interlock bars in adjacent dispensing device units with an opposite relative motion, said opposite motion of said sliding bar on adjacent dispensing device units locking a cam follower associated therewith into a notch in the rotating cam of said adjacent dispensing device unit, thereby preventing said dispensing device unit from being activated.

7. The interlock device of claim 6 in which at least one of an inboard or outboard end of said sliding bar has an adjustable extension.

8. The interlock device of claim 7 in which one inboard end and both outboard ends have an adjustable extension.

9. The interlock device of claim 6 in which butting of interlock bars on said adjacent dispensing apparatus is sufficient to prevent said vaporizer from being activated.

10. The interlock device of claim 6 in which the motion of the interlock bars on a first dispensing apparatus unit causes significant motion of the interlock bars on an adjacent dispensing apparatus unit such that a first crank on said adjacent dispensing apparatus unit rotates in a second direction which forces and locks a cam follower associated therewith into a notch in the rotating cam of said adjacent dispensing apparatus unit.

11. The interlock device of claim 6 which is adapted to be easily demountable and installed on existing anaesthetic apparatus.

* * * * *